(12) United States Patent
Vansant et al.

(10) Patent No.: US 6,265,625 B1
(45) Date of Patent: Jul. 24, 2001

(54) ISOLATION OF GLYCOLS

(75) Inventors: Frans Vansant, Kalmthout; Jozef de Hert, Antwerp, both of (BE); Dieter Köffer, Birkenau (DE); Gerhard Theis, Maxdorf (DE); Winfried Terjung, Dinslaken (DE)

(73) Assignee: BASF Aktiengesellschaft, Lidwigshafen (DE)

( * ) Notice: Subject to any disclaimer, the term of this patent is extended or adjusted under 35 U.S.C. 154(b) by 0 days.

(21) Appl. No.: 09/451,860

(22) Filed: Dec. 1, 1999

(30) Foreign Application Priority Data

Dec. 3, 1998 (DE) ................................. 198 55 911

(51) Int. Cl.[7] ............................ C07C 29/76; C07C 29/80
(52) U.S. Cl. ................ 568/868; 159/5; 159/6.1; 159/6.2; 159/11.2; 159/11.3; 568/866; 568/867; 568/869

(58) Field of Search ...................... 568/866, 867, 568/868, 869; 159/5, 6.1, 6.2, 11.2, 11.3

(56) References Cited

U.S. PATENT DOCUMENTS 4,822,926   4/1989   Dye ..................................... 568/867

FOREIGN PATENT DOCUMENTS 235635   5/1986   (DE) .

OTHER PUBLICATIONS

*Ullmann's Enc. of Ind. Chem.*, 5th Ed., vol. A10, p. 117–135.

Primary Examiner—Peter O'Sullivan
(74) Attorney, Agent, or Firm—Keil & Weinkauf

(57) ABSTRACT

This invention relates to a process for preparing and isolating glycols and to a thin-film evaporator which is used in carrying out the process.

11 Claims, 2 Drawing Sheets

ISOLATION OF GLYCOLS

The invention relates to a process for preparing and isolating glycols and to a thin-film evaporator which is used in carrying out the process.

Ethylene oxide (EO hereinafter) and ethylene glycol are important intermediates in industrial chemistry. Important secondary products of EO are, in particular, ethylene glycol, glycol ether, ethanolamines, ethylene carbonate and polyethoxylates. Ethylene glycol is predominantly used for preparing polyesters, polyurethanes, dioxane, plasticizers and as antifreeze.

EO is currently prepared on a large scale generally by direct oxidation of ethylene with molecular oxygen or air in the presence of silver oxide catalysts. A by-product of this highly exothermic reaction is carbon dioxide which is chiefly formed by total oxidation.

EO preparation processes which are carried out industrially are described, for example, in Ullmanns Encyclopedia of Industrial Chemistry, Fifth Edition, Carl Hanser Verlag (Munich), Volume A 10, pages 117ff. According to this, a currently standard EO reactor contains the fixed-bed catalyst in a tube bundle which has several thousand tubes through which the reaction mixture is conducted in a recirculated gas stream. As heat carrier, a boiling liquid, for example water, circulates between the tubes. Ethylene and oxygen are introduced in the recirculated gas stream which is passed through the reactor and comprises, in addition to the reactants, inert gases and the by-product of total oxidation of ethylene, carbon dioxide. The cooled reactor discharge is if appropriate first quenched with an NaOH solution in order to scrub out organic acids, in particular formic acid and acetic acid, and high-boiling minor components. These components can be discharged from the recirculated gas system via a "quench bleed". In an EO absorber, which is generally operated at approximately 16 bar and approximately from 25 to 40° C., the EO is scrubbed virtually completely out of the recirculated gas by a large scrubbing water stream (approximately 35 metric t of scrubbing water are required for the absorption of 1 metric t of EO from 25 metric t of recirculated gas). The pressure in the absorber is given here by the pressure in the recirculated gas system. Typically from 5 to 100 ppm of EO remain in the recirculated gas. After a potash scrubbing to remove carbon dioxide, the recirculated gas is again enriched with ethylene and oxygen and fed to the EO reactor. The aqueous solution produced in the absorber, in addition to approximately 3% by weight of EO, also comprises traces of the other components present in the recirculated gas. The EO is then desorbed from the loaded scrubbing water in an EO desorber (EO stripper). The resultant stripper vapors comprise approximately 50% by weight of water and approximately 50% by weight of EO and also the gases present in the loaded scrubbing water. The depleted scrubbing water, after cooling, is recycled to the EO desorber as cycle water. Since the EO is partly hydrolyzed to glycols in the EO desorber, these are discharged from the EO desorber via the glycol bleed. The desorber vapors are first condensed. The dissolved gases are then stripped from the condensate in a light-end tower and recycled to the recirculated gas system. The resultant gas-free approximately 50% strength aqueous EO solution is partly distilled in a distillation column to give pure EO or, after addition of water, is reacted in a glycol reactor to form an aqueous glycol solution.

The hydrolysis reactor is usually operated at from 120 to 250° C. and pressures of from 30 to 40 bar. The hydrolysis product is first dewatered (to a residual water content of from 100 to 200 ppm) and then separated into the various glycols in pure form. During the hydrolysis, monoethylene glycol is first predominantly formed, which can then in part further react with EO to form di-, tri- and polyethylene glycols. Since monoethylene glycol (for simplicity called ethylene glycol hereinafter) can in principle be the only glycol occurring in the entire process, the word glycols (in the plural) hereinafter can also mean solely monoethylene glycol (ethylene glycol).

The dewatering is generally performed in a cascade of towers of different pressure stages with decreasing pressure. For reasons of thermal integration, generally only the bottom reboiler of the first pressure tower is heated with external steam, and all other pressure towers are, in contrast, heated with the vapors of the respectively preceding tower. Depending on the water content of the hydrolysis reactor discharge and the pressure/temperature level of the external steam used in the bottom reboiler of the first tower, the pressure dewatering cascade consists of from 2 to 7 towers. A vacuum dewatering follows the pressure dewatering. The dewatered glycol mixture is fractionated into the pure substances in a plurality of towers. The products monoethylene glycol, di-, tri- and possibly tetraethylene glycol are each withdrawn as overhead product, and all other higher glycols are produced as bottom product of the last tower in the form of a mixture termed polyethylene glycols. The main product of this work-up is generally monoethylene glycol (ethylene glycol).

The EO-containing quench bleed cannot be disposed of as it is, because of the toxicity of EO. Furthermore, it is of economic interest to recover the valuable materials EO and glycol present. The EO can be desorbed in a quench bleed stripper, for example, and fed to the EO desorber. Alternatively, the EO in the quench bleed can be converted into glycols in a hydrolysis reactor at from 160 to 230° C. and pressures of from 20 to 35 bar. The resultant aqueous glycol solution can be disposed of without problem.

Alternatively, according to U.S. Pat. No. 4,822,926, the glycols can be recovered after concentrating them in a flasher and separating off salt in a centrifuge. A disadvantage of this method is the production of a solid which is generally more difficult to handle than liquids.

Since in the EO absorber-desorber water circuit the EO is in part hydrolyzed to glycols, a partial stream of the bottoms outflow of the EO desorber is discharged and concentrated, in which case the resultant vapors can be recycled to the EO desorber (described in DD-A-235 635). The concentrated glycol solution, the glycol bleed, is fed to a flasher where some of the glycols are recovered. The salt- and glycol-containing bottom stream is disposed of.

It is an object of the present invention to provide a process in which the glycols formed during the process are recovered as pure substances. In the process, the corresponding mixtures which, in addition to glycols, generally also comprise salts and water, are to be separated so that products of high quality are obtained. In addition, the process is to ensure that as far as possible all glycols are recovered, so that the residues which arise in the process and are to be disposed of are decreased. The method is to be effective and inexpensive.

We have found that this object is achieved by the process for isolating glycols from a liquid mixture comprising glycols, water and salts by (a) evaporating at least a partial amount of the water and glycols which are present in the mixture, separating off a liquid or gaseous medium which is freed from salt and comprises glycols and water, (b) dewatering the medium and (c) isolating the glycols from the dewatered medium.

The process of the invention comprises using a thin-film evaporator for carrying out stage (a).

In a preferred embodiment, the liquid mixture comprising glycols, water and salts arises during the work-up of a reaction mixture which results from the catalytic reaction of ethylene with oxygen and comprises EO, in which case, during the work-up, before the liquid mixture is formed, at least a partial amount of the EO is hydrolyzed to form ethylene glycol. According to the invention, a process is also provided for preparing glycols. In this process, by catalytically reacting ethylene with oxygen, an EO-containing reaction mixture is produced which is then worked up. In this case, a liquid mixture which comprises glycols, water and salts arises. The preparation process comprises separating this mixture according to the latter process (process for isolating glycols).

In addition, according to the invention, a thin-film evaporator is provided for carrying out stage (a) of the process for isolating glycols, which evaporator comprises the following apparatuses:

I. an outlet tube for the liquid or gaseous medium which arises at the top, is freed from salts and comprises glycols and water II. a bottom outflow, III. a feed, IV. a cleaning agent introduction tube, V. two inert gas introduction tubes, VI. a cleaning outflow, VII. an outflow vessel, VIII. a collecting vessel, IX. an outflow valve, X. a cleaning-water valve, XI. a vessel outflow valve, XII. a cleaning outflow valve and XIII. a vent valve.

The thin-film evaporator used to carry out stage (a) of the isolation process of the invention is generally operated at from 160 to 220° C., preferably from 180 to 200° C., with the pressure in the thin-film evaporator generally being from 30 to 200 mbar, preferably from 40 to 80 mbar.

In a preferred embodiment, the thin-film evaporator has a bottoms outflow system which is cleaned at intervals. Generally the bottoms outflow system is cleaned with water.

The glycols from the aqueous salt-containing solutions can be separated off effectively, inexpensively and in an environmentally friendly manner. These are especially glycols which arise during the work-up in a quench bleed concentrator (glycol content in the latter up to at least 50% by weight, preferably up to at least 80% by weight) and in a glycol bleed flasher. The liquid mixture which comprises glycols, water and salts and underlies the isolation process of the invention is preferably formed by combining the bottoms discharges of the quench bleed concentrator and the glycol bleed flasher. Generally, the liquid mixture comprising glycols, water and salts is free or virtually free (less than 0.1% by weight of EO is present) of EO. The content of glycols in the liquid mixture comprising glycols, water and salts is generally at least 50% by weight, preferably at least 80% by weight.

The vapors of the thin-film evaporator are condensed, producing (according to stage (a) of the isolation process of the invention) the liquid or gaseous medium which is freed from salt and comprises glycols and water and is fed to the vacuum dewatering of the main glycol stream. The salt-containing liquid residue from the thin-film evaporator is disposed of. The bottoms outflow system of the thin-film evaporator is cleaned here (generally at intervals with water) so that salt deposition is avoided. The operating conditions guarantee an optimum glycol recovery and problem-free operation of this process step. The amount of water required in order to remove the residue from the thin-film evaporator without problems can generally be restricted to from 10 to 20% of the amount of residue, so that the resultant residue mixture can be disposed of by incineration. However, the residue can also be disposed of in a biological treatment plant. In this case, it is not necessary to minimize the amount of water.

A preferred embodiment of the invention is described in more detail below:

Figure 1:
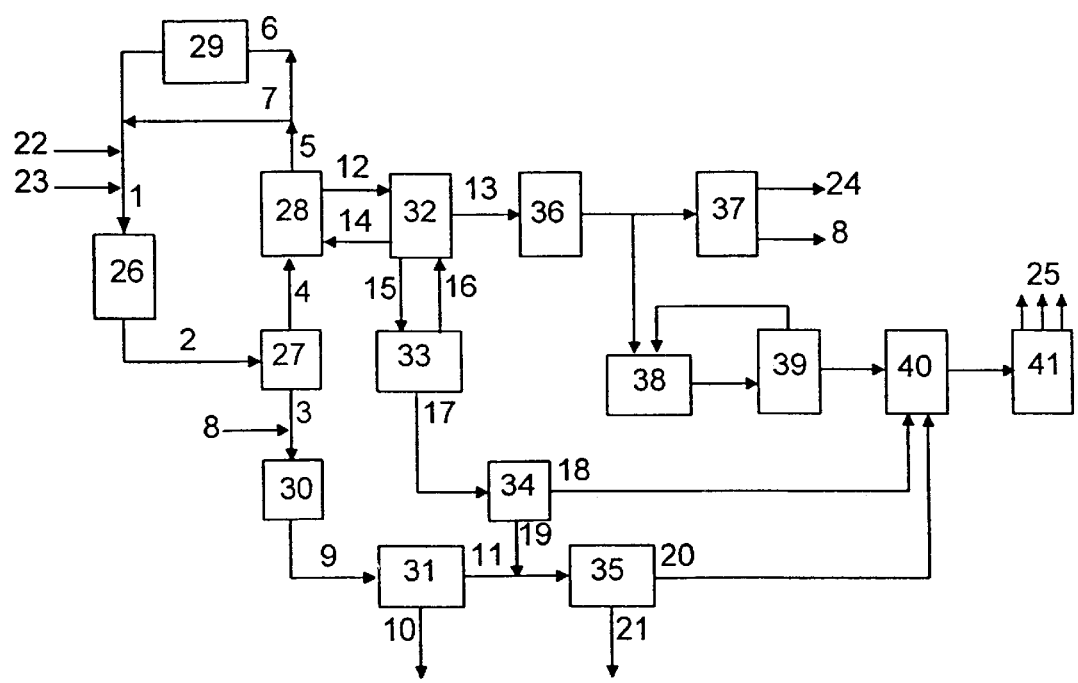
FIG. 1 of the drawing is a diagrammatic representation of an EO/glycol process. Machinery and apparatuses, such as pumps, heat exchangers and vessels, for example, which are not essential to describing the invention are not itemized.

Ethylene and oxygen are introduced in a recirculated gas 1 which, in addition to the reactants, comprises inert gases, for example nitrogen, the by-product of the total oxidation of ethylene, carbon dioxide and impurities of the reactants, for example ethane and argon. The reaction proceeds in a reactor 26 (or alternatively in a plurality of reactors) in the presence of a silver-containing catalyst. In addition to and the by-products of the total oxidation, carbon dioxide and water, small amounts of minor components such as acetaldehyde, formaldehyde and organic acids such as formic acid and acetic acid are also formed. The reactor discharge 2 is first cooled and then fed to a quench 27. In the quench 27, the majority of the reaction water formed condenses out. An NaOH solution is added to the quench recycle to scrub out the organic acids, especially formic acid and acetic acid. In addition, as a result some of the carbon dioxide is reacted, forming sodium salts. In principle, the salt formation can also be formed with other bases. The salts formed are especially bicarbonates, carbonates, formates and acetates. Some of the EO formed is likewise scrubbed out and a small part of the EO is converted into glycol. The quench recycle is customarily operated at from 25 to 50° C. and pressures of from 12 to 20 bar. Some of the quench recycle is discharged as quench bleed stream 3. A typical quench bleed comprises from 1 to 3% by weight of EO; from 1 to 3% by weight of glycol; from 0.2 to 1% by weight of sodium salts (especially sodium bicarbonate, sodium carbonate, sodium formate and sodium acetate), in addition relatively small amounts of minor components such as formaldehyde and acetaldehyde, and dissolved gases from the recirculated gas, for example ethylene and methane.

The reaction gas from quench 27 which has been purified in this manner is fed to the EO absorber 28, where the EO is virtually completely scrubbed out by a large water stream at from 25 to 45° C. and pressures of from 12 to 20 bar. The recirculated gas 5 which is freed from EO is divided into two streams. The first partial stream 6 is fed to a potash scrubber to remove carbon dioxide and is then combined with the second partial stream of the recirculated gas 7. After enrichment with ethylene and oxygen, all of the recirculated gas 1 is fed back to the EO reactor.

The dissolved gases in the quench bleed can first optionally be separated off in a flasher and fed, for example, to the EO desorber 32 or to the light-end tower 36. However, this is not absolutely necessary (and is therefore not shown in the figure, either).

The quench bleed is heated and then fed to a quench bleed hydrolysis reactor 30. The temperatures, pressures and residence times required are comparable with the operating parameters in the glycol reactor 38 for preparing glycols. It must be ensured that EO is completely converted into glycols and that no phase separation occurs. The process is particularly advantageous in a plant in which some of the EO is distilled to form pure EO, after which, in addition, the aldehyde-containing stream 8 from the pure EO distillation is fed to the quench bleed hydrolysis reactor 30.

The quench bleed reactor discharge 9 is concentrated in a quench bleed concentrator 31, the water being withdrawn as tops stream 10. Concentration expediently takes place in a distillation tower or in a cascade of towers of different pressure stages with thermal integration.

The quench bleed concentrator 31 is operated so that the glycol concentration in the bottoms discharge 11 is at least 50% by weight, preferably at least 80% by weight.

The aqueous EO solution 12 arising in the EO absorber 28 is fed to an EO desorber 32 in which the EO is desorbed from the loaded scrubbing water. The stripper vapors 13 arising comprise approximately 50% by weight of water and approximately 50% by weight of EO and also the gases present in the loaded scrubbing water. The depleted scrubbing water 14, after cooling, is recycled as cycle water to the EO absorber 28. Since some of the EO is hydrolyzed to form glycols in the EO absorber-desorber circuit, a partial stream 15 of the bottoms outflow of the EO desorber is discharged and concentrated in the glycol bleed concentrator 33, the resultant vapors 16 being recycled to the EO desorber 32. The concentrated glycol solution, the glycol bleed 17, is fed to the glycol bleed flasher 34.

The glycol bleed concentrator 33 is usually operated at from 130 to 140° C. and pressures of from 1.5 to 2.5 bar. The glycol concentration of the bottoms outflow is preferably from 40 to 60% by weight. The glycol bleed 17 is fed to the glycol bleed flasher 34 in which water and glycol are vaporized. The tops stream 18 of the glycol bleed flasher is preferably fed in the vapor state to the apparatus for glycol vacuum dewatering 40. The glycol bleed flasher 34 is usually operated at from 110 to 140° C. and pressures of from 300 to 400 mbar. The bottoms discharge of the glycol bleed flasher 19 is mixed with the bottoms discharge of the quench bleed concentrator 11 and fed to the thin-film evaporator 35.

Thin-film evaporation is used for continuous distillation, in particular for vaporizing heat-sensitive substances from high-boiling residues and for concentrating heat-labile substances. In this case, the liquid is distributed by trickling (falling-film evaporator), the action of centrifugal force (special embodiment of a rotary evaporator), specially constructed scrapers (filmtruders) or other methods, of to form thin films (the film thickness is generally of the order of magnitude of approximately 0.1 mm) on the (generally) heated surfaces. Thin liquid films enable rapid evaporation, so that the components present are exposed only briefly to the (generally) relatively high temperatures in the evaporator. The residence time, the temperature and the pressure (vacuum) are designed in accordance with the respective separation objective. To protect the substances in question, temperatures as low as possible and residence times as short as possible are to be preferred here. In addition to apparatuses which are called thin-film evaporators in general technical usage, according to the invention all evaporation apparatuses which operate according to the above-described principle are understood as being thin-film evaporators.

A thin-film evaporator proves to be particularly suitable for separating a salt-containing glycol solution into a salt-free vaporous glycol-water mixture (this is removed via the outlet tube 20) and a highly concentrated salt-containing bottoms outflow 21. A thin-film evaporator of this type operates at from 160 to 220° C., preferably from 180 to 200° C. and at pressures of from 40 to 200 mbar, preferably from 60 to 90 mbar. A mild separation by thin-film evaporation is therefore expedient, since glycols, in the presence of oxygen and/or salts present, readily form by-products which reduce quality, in particular if the glycols are exposed to relatively high temperatures for a relatively long time.

The bottoms outflow 21 of the thin-film evaporator 35 generally comprises from 10 to 30% by weight, preferably from 15 to 25% by weight, salts. A mixture of the two above-described bleed streams (firstly the bottoms discharge of the quench bleed concentrator 11 and secondly the bottoms discharge of the glycol bleed flasher 19) can be particularly effectively separated in a thin-film evaporator 35. The bottoms outflow 21 of the thin-film evaporator 35 can, after mixing with from 10 to 20% by weight of water, be pumped off and stored. The mixture is suitable for being burnt in a residue incinerator. It is likewise possible to dispose of this mixture in a biological treatment plant. In this case it is not necessary to minimize the amount of water. The vaporous glycol/water mixture, after condensation, is fed to the apparatus for glycol vacuum dewatering 40. The dewatered glycol mixture is then separated into the corresponding products by distillation (in apparatus 41).

Technical Design of the Thin-film Evaporator 35:

Thin-film evaporators are usually used, as already described at the outset, for distilling and concentrating heat-sensitive substances. A typical thin-film evaporator 35 which can be used according to the invention has a vertically upright, externally heated tube on the inner surface of which the product to be vaporized is spread as a thin film by a rotor. The product enters the evaporator above the heating zone and, as a result of the mechanical distribution by the rotor, flows as a liquid film over the heated surface. The low-boiling components vaporize, while the residue drains downward. The vapors flow through a demister which is situated in the top of the evaporator and are condensed in a separately disposed condenser. To heat the evaporator surface, a jacket is provided in which heating with heating steam takes place. For the mechanical distribution of liquid, a rotor having pendulous metal scraper blades is installed. During operation, the centrifugal force presses the scraper blades against the evaporator wall which causes a uniform product distribution and an intensive liquid mixing of the liquid film.

The thin-film evaporator is not only intended to ensure the virtually complete vaporization (tri- and tetraglycols are vaporized with difficulty: a virtually complete vaporization therefore generally relates to about 10% of the glycols remaining in the bottoms) of the glycols from the glycol- and salt-containing solution, but also to provide the salts (especially sodium bicarbonate, sodium carbonate, sodium formate and sodium acetate) as a pumpable mixture. However, in the case, of a thin-film evaporator which operates according to the abovementioned principle, this is not the case since salts can deposit in the region of the outflow and cause encrustations, so that the bottoms discharge, owing to blockages, can no longer be carried out without problems. The continuous operation of the thin-film evaporation must be stopped when such blockages occur so that appropriate cleaning work can be initiated.

Figure 2:
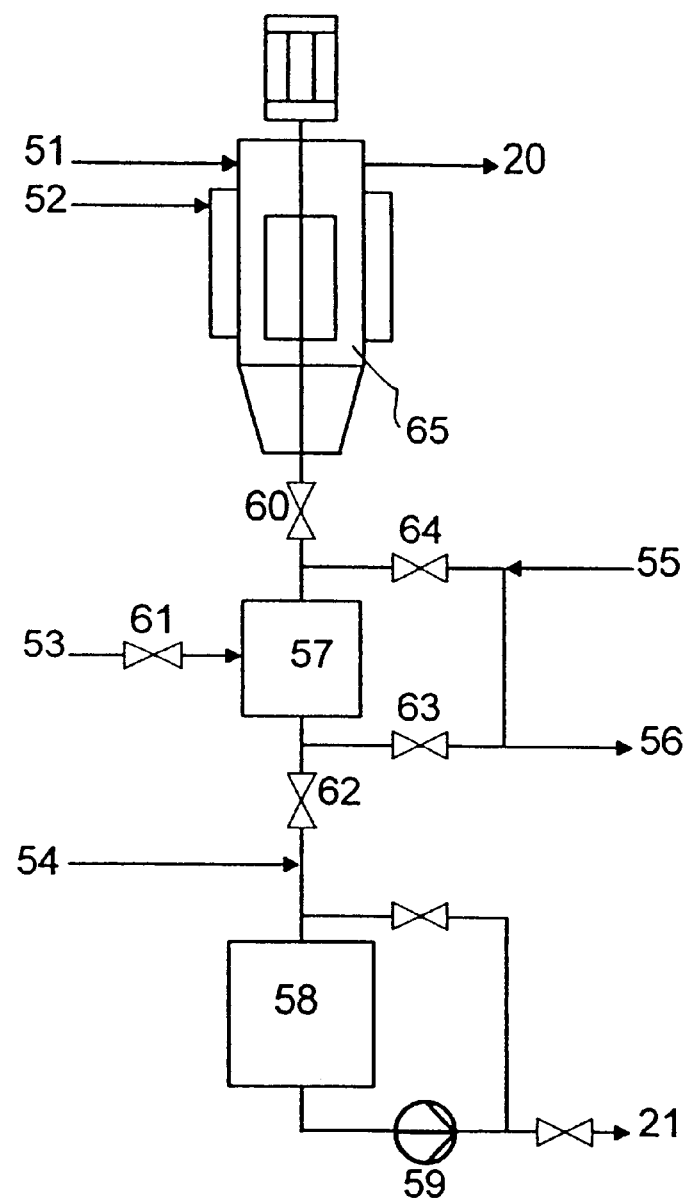

To avoid the bottoms discharge system from being blocked by salts crystallizing out, in a preferred embodiment the outflow line is cleaned at intervals by means of a special cleaning apparatus (this is shown in FIG. 2 of the drawing). For this purpose, the bottoms outflow is first collected in an outflow vessel 57 which gradually fills up. After a certain filling height is reached, the outflow valve 60 is closed and the vacuum in the outflow vessel 57 is eliminated by opening the vessel outflow valve 62 to the collection vessel 58 (the collection vessel 58 is under atmospheric pressure or slight super atmospheric pressure). The vent valve 64 is then opened and the contents of the outflow vessel 57 drain into the collection vessel 58. The contents of the collection vessel 58 are expediently circulated using a pump 59 in order to keep them homogenous and to prevent possible salt deposition. The contents are removed continuously or batchwise for intermediate storage and further utilization, for example combustion.

The outflow vessel 57 is then cleaned. Expediently, water is used for this purpose, preferably warm water or steam condensate. To initiate the cleaning operation, the vessel outflow valve 62 is closed, and the cleaning outflow valve 63 and the cleaning water valve 61 are opened. The warm cleaning water which is fed via the cleaning agent introduction tube 53 then flows through the outflow vessel 51 and in this manner removes salt deposits. The cleaning outflow can be fed without problems to a biological treatment plant. Cleaning duration and water flow rate are set as required so that the amount of water required is as small as possible. Depending on the loading of the thin-film evaporator 35 and salt content, an amount of water from 10 to 50l and a cleaning time from 1 to 2 minutes are sufficient. To prevent blockages in the outflow line to the collection vessel 58, this line is periodically cleaned by opening the vessel outflow valve 62 (instead of the cleaning outflow valve 63). Preferably, this is performed every 10 or 20 cleaning passes.

After a precleaning time has passed, the cleaning outflow valve 63 is closed and in the further course of the cleaning phase the water is flushed via the outflow vessel 57 and the outflow line through the vent line and through the vent valve 64. The cleaning water valve 61 is then closed and, in order to empty the outflow vessel, the cleaning outflow valve 63 is opened. Remaining cleaning water is drained by opening the vessel outflow valve 62. All valves are then closed again.

By opening the outflow valve 60, the outflow vessel is evacuated again and the outflow cycle can begin again.

To avoid the ingress of air, the outflow lines to the collection vessel and to the cleaning agent outflow are provided with inert gas purging (generally nitrogen purging). Inert gas is fed via the introduction tube (54; 55).

Automatic sequence control of these outflow and cleaning processes is advantageous.

EXAMPLE

The table below summarizes the data of a preferred process for the large-scale production of EO and glycols in a coupled plant operating according to the invention. The values apply to a plant having a capacity of 300,000 metric t of EO per year, of which 100,000 metric tons per year are distilled to form pure EO and the remaining EO is converted into approximately 275,000 metric tons of glycols per year.

The results reported in the table make it clear that the novel work-up of the quench bleed and glycol bleed streams proceeds effectively. The total losses of the quench bleed and glycol bleed streams are only 0.12% by weight, converted to be based on EO. The materials of value in the bleed streams are fed to the main glycol stream and thus pass into the pure glycols.

TABLE

| Stream No. | | Quench bleed stream 3 | Aldehyde discharge from pure EO distillation 8 | Quench bleed reactor discharge 9 | Tops stream quench bleed concen-trator 10 | Bottoms discharge quench bleed concen-trator 11 | Bottoms discharge glycol bleed flasher 19 | Tops stream thin-film evaporator 20 | Bottoms outflow thin-film evaporator 21 |
|---|---|---|---|---|---|---|---|---|---|
| Temp. | °C. | 40 | 30 | 220 | 102 | 135 | 130 | 130 | 190 |
| State | | liquid | liquid | liquid | gaseous | liquid | liquid | gaseous | liquid |
| Water | % by wt. | 95.7 | 29.0 | 89.5 | 99.8 | 15..3 | 3.9 | 12.6 | 0.1 |
| EO | % by wt. | 3.0 | 70.0 | 0.0 | 0.0 | 0.0 | 0.0 | 0.0 | 0.0 |
| Glycols | % by wt. | 1.0 | 0.0 | 10.1 | 0.1 | 83.0 | 95.9 | 87.4 | 79.8 |
| Sodium salts | % by wt. | 0.2 | 0.0 | 0.2 | 0.0 | 1.7 | 0.2 | 0.0 | 20.0 |
| Others | % by wt. | 0.1 | 1.0 | 0.1 | 0.1 | 0.0 | 0.1 | 0.0 | 0.1 |
| Total | % by wt. | 100 | 100 | 100 | 100 | 100 | 100 | 100 | 100 |
| Total stream | kg/h | 7000 | 400 | 7400 | 6500 | 900 | 400 | 1219 | 81 |
| Water | kg/h | 6699.00 | 116.00 | 6624.90 | 6487.15 | 137.75 | 15.60 | 153.27 | 0.08 |
| EO | kg/h | 210.00 | 280.00 | 0.00 | 0.00 | 0.00 | 0.00 | 0.00 | 0.00 |
| Glycols | kg/h | 70.00 | 0.00 | 750.10 | 3.25 | 746.85 | 383.40 | 1065.61 | 64.64 |
| Sodium salts | kg/h | 15.40 | 0.00 | 15.40 | 0.00 | 15.40 | 0.80 | 0.00 | 16.20 |
| Others | kg/h | 5.60 | 4.00 | 9.60 | 9.60 | 0.00 | 0.20 | 0.12 | 0.08 |
| Total | kg/h | 7000.00 | 400.00 | 7400.00 | 6500.00 | 900.00 | 400.00 | 1219.00 | 81.00 |

Others = other components

LIST OF DESIGNATIONS

1 Recirculated gas stream introduced into the reactor
2 Stream discharged from the reactor
3 Quench bleed stream
4 Purified reaction gas stream originating from the quench
5 Stream of recirculated gas freed from EO, removed from the EO absorber
6 Recirculated gas stream fed to the potash scrubber
7 Second recirculated gas partial stream
8 Aldehyde-containing stream from pure EO distillation
9 Quench bleed reactor discharge stream
10 Tops stream of the quench bleed concentrator
11 Bottoms discharge of the quench bleed concentrator
12 Aqueous EO solution produced in the EO absorber
13 Stripper vapors
14 Depleted scrubbing water 15 Partial steam of the bottoms outflow of the EO desorber
16 Vapor stream of the glycol bleed concentrator
17 Glycol bleed
18 Tops stream of the glycol bleed flasher
19 Bottoms discharge of the glycol bleed flasher
20 Outlet tube for the liquid or gaseous medium which arises at the top of the thin-film evaporator, is freed from salts and comprises glycols and water
21 Bottoms outflow of the thin-film evaporator
22 Ethylene introduction tube
23 Oxygen introduction tube
24 Pure EO outlet tube
25 Pure glycols outlet tube
26 Reactor for preparing EO
27 Quench
28 EO absorber
29 Potash scrubber
30 Quench bleed hydrolysis reactor
31 Quench bleed concentrator
32 EO desorber
33 Glycol bleed concentrator
34 Glycol bleed flasher
35 Thin-film evaporator
36 Light-end tower
37 Tower for distillation of pure EO
38 Glycol reactor
39 Glycol pressure dewatering apparatus
40 Glycol vacuum dewatering apparatus
41 Apparatus for distilling the dewatered glycol mixture
51 Feed into the thin-film evaporator
52 Steam stream for heating the reactor jacket
53 Cleaning agent introduction tube
54 Inert gas introduction tube
55 Inert gas introduction tube
56 Cleaning outflow
57 Outflow vessel
58 Collection vessel
59 Pump
60 Outflow valve
61 Cleaning water valve
62 Vessel outflow valve
63 Cleaning outflow valve
64 Vent valve
65 Interior of the thin-film evaporator

We claim:

1. A process for isolating glycols from a liquid mixture comprising glycols, water and salts by
   (a) evaporating at least a partial amount of the water and glycols which are present in the mixture, separating off a liquid or gaseous medium which is freed from salt and comprises glycols and water,
   (b) dewatering the medium and
   (c) isolating the glycols from the dewatered medium,
which comprises using a thin-film evaporator for carrying out stage (a).

2. A process as claimed in claim 1, wherein the liquid mixture comprising glycols, water and salts arises in the work-up of a reaction mixture which comprises EO and results from the catalytic reaction of ethylene with oxygen and, during the work-up, before the liquid mixture is formed, at least a partial amount of the EO is hydrolyzed to form ethylene glycol.

3. A process as claimed in claim 2, wherein, during the work-up, glycols arise in a quench bleed concentrator and in a glycol bleed flasher and wherein the liquid mixture comprising glycols, water and salts is formed by combining the bottoms discharges of the quench bleed concentrator and the glycol bleed flasher.

4. A process as claimed in claim 1, wherein the liquid mixture comprising glycols, water and salts is free or virtually free of EO.

5. A process as claimed in claim 1, wherein the content of glycols in the liquid mixture comprising glycols, water and salts is at least 50% by weight, preferably at least 80% by weight.

6. A process as claimed in claim 1, wherein the thin-film evaporator (35) used to carry out stage (a) is operated at from 160 to 220° C., preferably from 180 to 200° C.

7. A process as claimed in claim 1, wherein the pressure present in the thin-film evaporator is from 30 to 200 mbar, preferably from 40 to 80 mbar.

8. A process as claimed in claim 1, wherein the thin-film evaporator has a bottoms outflow system which is cleaned at intervals.

9. A process as claimed in claim 8, wherein the bottoms outflow system is cleaned with water.

10. A process for preparing glycols by catalytic reaction of ethylene with oxygen with the formation of a reaction mixture comprising EO and subsequent work-up of the reaction mixture, in which a liquid mixture comprising glycols, water and salts is produced, which comprises separating this mixture according to the process as claimed in claim 1.

11. A thin-film evaporator for carrying out stage (a) as claimed in claim 1, comprising the following apparatuses:
   I. an outlet tube for the liquid or gaseous medium which arises at the top, is freed from salts and comprises glycols and water,
   II. a bottoms outflow,
   III. a feed,
   IV. a cleaning agent introduction tube,
   V. two inert gas introduction tubes,
   VI. a cleaning outflow,
   VII. an outflow vessel,
   VIII. a collecting vessel,
   IX. an outflow valve,
   X. a cleaning-water valve,
   XI. a vessel outflow valve,
   XII. a cleaning outflow valve and
   XIII. a vent valve.

* * * * *